United States Patent [19]

Gram

[11] 4,113,959

[45] Sep. 12, 1978

[54] METHOD FOR RESOLVING AMINO AND AMMONIUM COMPOUNDS

[75] Inventor: Donald J. Gram, Los Angeles, Calif.

[73] Assignee: The Regents of the University of California, Berkeley, Calif.

[21] Appl. No.: 806,054

[22] Filed: Jun. 13, 1977

Related U.S. Application Data

[60] Division of Ser. No. 672,211, Mar. 31, 1976, Pat. No. 4,043,979, which is a continuation-in-part of Ser. No. 448,333, Mar. 5, 1974, Pat. No. 4,001,279, which is a continuation-in-part of Ser. No. 346,089, Mar. 29, 1973, abandoned.

[51] Int. Cl.$^2$ ............... C07C 101/02; C07C 101/72
[52] U.S. Cl. .................................. 560/38; 560/39; 260/501.11; 562/402
[58] Field of Search ............. 260/518 R, 518 A, 519, 260/543 R, 543 S, 501.11; 560/38, 39

[56] References Cited

U.S. PATENT DOCUMENTS

| | | | |
|---|---|---|---|
| 3,225,118 | 12/1965 | DeHelio | 260/47 UP |
| 3,336,259 | 8/1967 | Zimmerman et al. | 260/47 UP |
| 3,682,872 | 8/1972 | Briyzolora et al. | 260/47 UP |

*Primary Examiner*—Bernard Helfin
*Assistant Examiner*—James H. Reamer
*Attorney, Agent, or Firm*—John T. Reynolds

[57] ABSTRACT

Chiral, hinged, asymmetric host binaphthyl-based multiheteromacrocycles of oxygen covalently bonded to styrene/divinylbenzene copolymers are provided. These new compounds have specific chiral recognition properties, which properties make these new compounds useful for separating or resolving racemic and other mixtures of amino acids, amino acid esters and salts thereof for either or both of analytical purposes or large scale manufacturing procedures.

5 Claims, No Drawings

METHOD FOR RESOLVING AMINO AND AMMONIUM COMPOUNDS

Work on this invention was supported in part by the U.S. Public Health Service Research Grant No. GM 12640-12 from the Department of Health, Education and Welfare and by a grant from the National Science Foundation, GP 33533X.

CROSS REFERENCES

This is a divisional application of Ser. No. 672,211, filed Mar. 31, 1976 now U.S. Pat. No. 4,043,979, issued Aug. 23, 1977 which is a continuation-in-part of application Ser. No. 448,333, filed Mar. 5, 1974 now U.S. Pat. No. 4,001,279 which is a continuation-in-part of application Ser. No. 346,089, filed Mar. 29, 1973 and now abandoned.

INTRODUCTION

This invention relates to chiral, hinged, asymmetric host multiheteromacrocycles of the oxygen type which are useful to afford selective complexation of specific guest substances. More particularly, this invention provides such compounds covalently bound to a styrene/divinylbenzene copolymer.

BACKGROUND OF THE INVENTION

The present invention relates to a method for resolving chemical enantiomers selected from the group consisting of alkylammonium salts, amino acids and esters and salts thereof which comprises passing a liquid containing the mixed enantiomers through a styrene/divinylbenzene resin-bound host compound of the formula

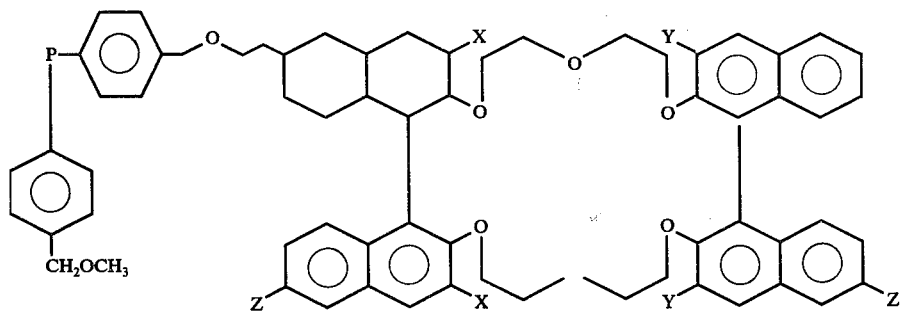

wherein P is the backbone of a solid styrene/divinylbenzene copolymer, each Z is H or $CH_2CH_2OH$, each X is either H or $CH_3$, each Y is either H or $CH_3$, and the binaphthyl groups of the macrocycle are in the (RR)- or (SS)- configurations, and recovering the separated enantiomers, and for which essential material constituting disclosure therefor is incorporated by reference here from Ser. No. 672,211, filed Mar. 31, 1976, now U.S. Pat. No. 4,043,979 issued Aug. 23, 1977.

CONCLUSIONS

The styrene-divinylbenzene polymer-host compounds of this invention are useful for separating or optically resolving racemic and other mixtures of chemical compounds which contain a primary amino group primarily in a position alpha or beta to a chiral center, e.g., racemic and other mixtures of such amino acids where only one of the optical isomers is useful for preparing dietary and medicinal compounds for animals including humans. These new polymer-host compounds can also be used in analytical procedures for determining optical purity of amines or amino acids, and the like. They can also be used for analyzing what kind and how much of each of the several amino acids is present in a protein hydrolysate. They can be used for determining the absolute configurations of compounds of yet unknown structural configurations.

This invention thus provides a method for resolving chemical enantiomers selected from the group consisting of alkylammonium salts, amino acids and esters and salts of such amino acids, preferably those which contain a primary amino group in a position alpha or beta to a chiral center which comprises passing a liquid solution or mixture containing the mixed enantiomers through a styrene/divinylbenzene resin-bound host compound of formula (III), above, and then recovering the separated enantiomers therefrom, by known procedures. The method of this invention is especially applicable for resolving alpha or beta amino acid compounds, such as the enantiomers of salts of phenylglycine, the d-isomer of which is useful as a reactant forming cephalexin, cephaloglycin and ampicillin antibiotics.

I claim:

1. A method for resolving chemical enantiomers selected from the group consisting of amino carboxylic acids and their esters and the alkylammonium salts thereof which comprises passing a liquid containing the mixed enantiomers through a styrene/divinylbenzene resin-bound host compound of the formula

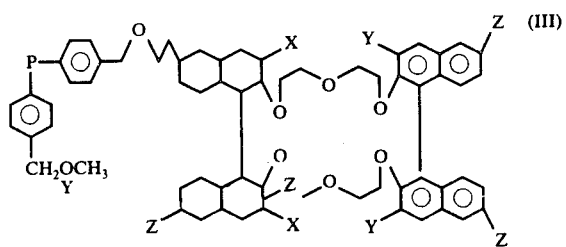

wherein P is the backbone of a solid styrene/divinylbenzene copolymer, each Z is H or $CH_2CH_2OH$, each X is either H or $CH_3$, each Y is either H or $CH_3$, and the binaphthyl groups of the macrocycle are in the (RR)- or (SS)- configurations, and recovering the separated enantiomers.

2. A method as defined in claim 1 wherein the chemical carboxylic enantiomers to be resolved are alpha or beta amino carboxylic acid or ester compounds thereof.

3. A method as defined in claim 1 wherein the chemical enantiomers to be resolved are salts of phenylglycine or of p-hydroxyphenylglycine.

4. A method as defined in claim 1 wherein the chemical enantiomers to be resolved are amino carboxylic acid ester salts.

5. A method as defined in claim 4 wherein the chemical enantiomers to be resolved are methyl esters of phenyl glycine salts or p-hydroxyphenylglycine salts.

* * * * *

UNITED STATES PATENT OFFICE
CERTIFICATE OF CORRECTION

Patent No. 4,113,959  Dated September 12, 1978

Inventor(s) Donald J. Cram

It is certified that error appears in the above-identified patent and that said Letters Patent are hereby corrected as shown below:

Title Page, Column on left, "Inventor: Donald J. Gram," should read -- Inventor: Donald J. Cram, --. Column 1, lines 35 to 52, the formula, "

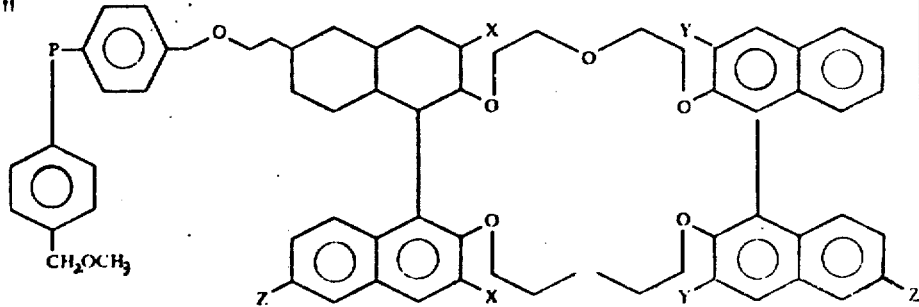

should read --

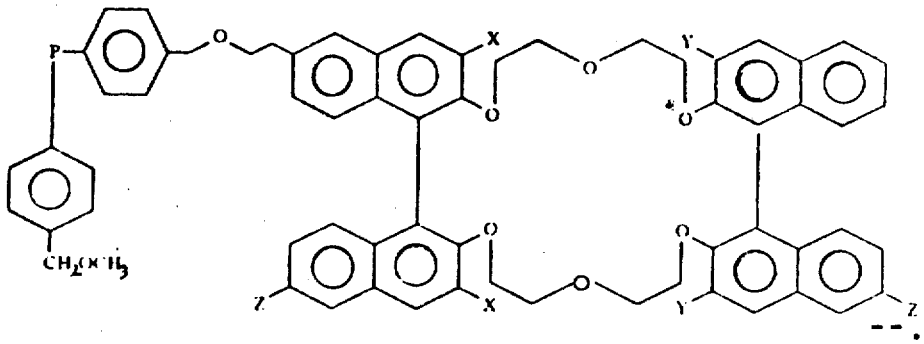

--.

Column 2, lines 52 to 59, structure

UNITED STATES PATENT OFFICE

CERTIFICATE OF CORRECTION

Patent No. 4,113,959   Dated September 12, 1978

Inventor(s) Donald J. Cram

It is certified that error appears in the above-identified patent and that said Letters Patent are hereby corrected as shown below:

" 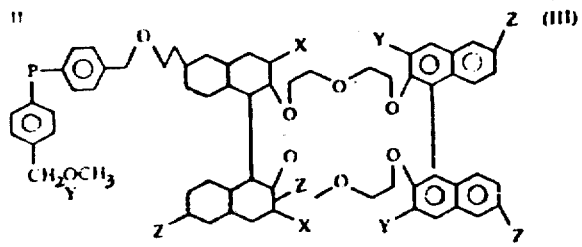 " should read

-- 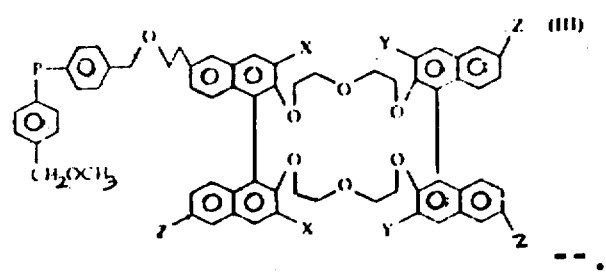 --.

Signed and Sealed this

Ninth Day of January 1979

[SEAL]

Attest:

RUTH C. MASON
Attesting Officer

DONALD W. BANNER
Commissioner of Patents and Trademarks